United States Patent
Ueno et al.

(10) Patent No.: US 6,755,914 B2
(45) Date of Patent: Jun. 29, 2004

(54) CRYSTALLINE MIXTURE SOLID COMPOSITION AND PREPARATION THEREOF

(75) Inventors: Ryuzo Ueno, Nishinomiya (JP); Akihiko Tabata, Kawanishi (JP); Junya Honda, Nishinomiya (JP); Yojiro Furukawa, Itami (JP); Sho Arai, Nishinomiya (JP)

(73) Assignee: Kabushiki Kaisha Ueno Seiyaku Oyo Kenkyusho, Osaka (JP)

( * ) Notice: Subject to any disclaimer, the term of this patent is extended or adjusted under 35 U.S.C. 154(b) by 15 days.

(21) Appl. No.: 10/030,981

(22) PCT Filed: May 17, 2001

(86) PCT No.: PCT/JP01/04101

§ 371 (c)(1),
(2), (4) Date: Jan. 16, 2002

(87) PCT Pub. No.: WO01/89323

PCT Pub. Date: Nov. 29, 2001

(65) Prior Publication Data

US 2003/0101989 A1 Jun. 5, 2003

(30) Foreign Application Priority Data

May 22, 2000 (JP) ........................................ 2000-150343

(51) Int. Cl.$^7$ ............................. C08B 30/00; C13J 1/06; C13D 3/00; C07H 1/00; C07G 17/00
(52) U.S. Cl. ............................. 127/29; 127/30; 127/42; 127/46.1; 127/52; 127/58; 536/1.11; 536/123.13; 536/124; 536/127
(58) Field of Search ............................. 127/29, 30, 42, 127/46.1, 58, 53; 536/1.11, 123.13, 124, 127

(56) References Cited

U.S. PATENT DOCUMENTS

| 4,684,720 A | | 8/1987 | Darsow et al. ............. 536/124 |
| 5,162,517 A | * | 11/1992 | Darsow ....................... 536/124 |
| 5,578,339 A | * | 11/1996 | Kunz et al. .................. 426/658 |
| 6,103,894 A | * | 8/2000 | Degelmann et al. ......... 536/124 |
| 6,146,856 A | * | 11/2000 | Heikkila et al. ............. 435/100 |
| 6,180,143 B1 | * | 1/2001 | Rapp et al. .................... 426/3 |
| 6,204,378 B1 | * | 3/2001 | Duflot et al. ................ 536/125 |
| 6,414,138 B1 | * | 7/2002 | Degelmann et al. ......... 536/124 |
| 6,458,400 B1 | * | 10/2002 | Willibald-Ettle et al. ... 426/548 |
| 2002/0028276 A1 | * | 3/2002 | Rapp et al. .................. 426/548 |

FOREIGN PATENT DOCUMENTS

| EP | 0-152779 A2 | | 8/1985 | ........... C07H/15/04 |
| EP | 0-625-578 A1 | | 11/1994 | ........... C12P/19/24 |
| EP | 1172370 | * | 1/2002 | ........... C07H/15/04 |
| JP | 60-181094 | | 9/1985 | ........... C07H/15/04 |
| JP | 62-148496 | | 7/1987 | ........... C07H/15/04 |
| JP | 07-051079 | | 2/1995 | ........... C12P/19/02 |
| JP | 07-241174 | | 9/1995 | ............. A23L/1/03 |

OTHER PUBLICATIONS

Schiweck, H., Palatinit—Herstellung, technologische Eigenschaften und Analytik palatinithaltiger Lebensmittel, "Alimenta" No. 19, pp. 5–16 (1980), no month available.

* cited by examiner

Primary Examiner—Mark L. Bell
Assistant Examiner—Patricia L. Hailey
(74) Attorney, Agent, or Firm—Sherman & Shalloway (57) ABSTRACT

A crystalline mixture solid composition comprising α-D-glucopyranosyl-1,1-mannitol (GPM), α-D-glucopyranosyl-1,6-sorbitol (GPS-6) and a small amount of α-D-glucopyranosyl-1,1-sorbitol (GPS-1) and a production process therefor. The above crystalline mixture solid composition is produced by mixing a hydrophilic solvent with a solid composition or aqueous solution comprising 50 to 80 wt % of GPM, 1 to 50 wt % of GPS-6 and 0.01 to 20 wt % of GPS-1, separating solid matter from a liquid, and removing water and the solvent from the solid matter and can be obtained as a thin scale crystal.

27 Claims, 5 Drawing Sheets

CRYSTALLINE MIXTURE SOLID COMPOSITION AND PREPARATION THEREOF

BACKGROUND OF THE INVENTION

1. Field of the Invention

The present invention relates to a crystalline mixture solid composition which comprises α-D-glucopyranosyl-1,1-mannitol and α-D-glucopyranosyl-1,6-sorbitol and/or a small amount of α-D-glucopyranosyl-1,1-sorbitol and to a production process therefor.

2. Prior Art

Hydrogenated isomaltulose (hydrogenated palatinose) has been known as one of low-calorie sweeteners which do not cause a carious tooth. The hydrogenated isomaltulose is a mixture of two sugar alcohols, that is, an almost equimolar mixture of α-D-glucopyranosyl-1,1-mannitol (to be abbreviated as GPM hereinafter) and its isomer α-D-glucopyranosyl-1,6-sorbitol (to be abbreviated as GPS-6 hereinafter), which can be obtained by forming isomaltulose (palatinose) from cane sugar by means of a transferase and then hydrogenating the palatinose.

The hydrogenated isomaltulose is known as an extremely useful sweetener which exhibits an excellent sweet taste like cane sugar, has low hygroscopicity, heat resistance, acid resistance, alkali resistance, excellent processability such as tablettability and granulability, and physiological properties such as low calorie, noncariogenic properties and insulin non-irritating properties.

As the method of crystallizing the hydrogenated isomaltulose, H. Schiweck's report (Alimenta. 19,5-16, 1980) discloses a vacuum crystalizar process. However, this process is very complicated and repeats the steps of evaporation, aging and centrifugation, thereby consuming a huge amount of energy and boosting product costs.

JP-A 60-181094 (the term "JP-A" as used herein means an "unexamined published Japanese patent application") discloses a process for crystallizing an aqueous solution of hydrogenated isomaltulose having a solid content of about 80% in a vacuum crystallization apparatus. However, since this process requires a special apparatus such as a vacuum crystallization apparatus and employs a batch system, it is not practical due to its low production efficiency.

JP-A 62-148496 discloses a process for crystallizing hydrogenated isomaltulose in accordance with a kneading method using seed crystals. This process is used to crystallize mainly a GPM component out of hydrogenated isomaltulose components. That is, the water content of the hydrogenated isomaltulose is adjusted to a range of more than 5% and 20% or less, the liquid temperature is maintained at a range of 50 to 90° C. according to the content of water, seed crystals are added and mixed, and the mixed product is solidified by cooling the temperature at around room temperature, dried and ground to obtain crystallized hydrogenated palatinose powders. However, this process has a problem with processing (such as grindability) as the kneaded product obtained by this process has high stickiness and also a problem with distribution (such as caking and the propagation of microorganisms) as cooling and drying take long time.

It is also known that when a transferase is caused to act on cane sugar, trehalulose (α-D-glucopyranosyl-1,1-fructose) is formed in addition to isomaltulose. Generally speaking, when hydrogenated isomaltulose is produced, after only isomaltulose is obtained by crystallization separation, the residual mixture containing trehalulose is discarded or disposed at a low cost. It is known that trehalulose is converted into GPM and α-D-glucopyranosyl-1,1-sorbitol (to be abbreviated as GPS-1) by hydrogenation. That is, when a transferase is caused to act on cane sugar as a raw material and the obtained mixture is hydrogenated, a mixture of GPM, GPS-6 and GPS-1 can be obtained. To obtain such a mixture, a process is known as disclosed in JP-A 7-51079. This process comprises the first step of carrying out the conversion reaction of cane sugar, the second step of removing unreacted cane sugar and the third step of carrying out a hydrogenation reaction in the presence of a catalyst. As for solidification, the above publication discloses a fine particulate product obtained by vaporizing water for solidification and grinding. However, the product is an amorphous and glass-like solid, has high hygroscopicity, and is difficult to handle and easily worn by abrasion during circulation. Generally speaking, when the content of a honey portion (GPS-1 and the residual sugars in the present invention) in a crystalline mixture solid is high, the product has high moisture absorption and is difficult to handle. Consequently, a crystalline mixture solid composition which has a low content of the honey portion and excellent handling ease and can be produced at a low cost has been desired.

SUMMARY OF THE INVENTION

It is an object of the present invention to provide a crystalline mixture solid composition which rarely has moisture absorption, is easy to handle and dissolve, and comprises GPM and GPS-6 and/or a small amount of GPS-1 in an extremely short period of time with small-scale equipment by a process which can save power and does not take much time and labor.

It is another object of the present invention to provide an industrially advantageous process for producing the above crystalline mixture solid composition of the present invention.

Other objects and advantages of the present invention will become apparent from the following description.

According to the present invention, firstly, the above objects and advantages of the present invention are attained by a crystalline mixture solid composition which comprises α-D-glucopyranosyl-1,1-mannitol, α-D-glucopyranosyl-1,6-sorbitol and 0.01 to 1.99 wt % of α-D-glucopyranosyl-1,1-sorbitol (the above wt % is based on the total weight of the α-D-glucopyranosyl-1,1-mannitol, α-D-glucopyranosyl-1,6-sorbitol and α-D-glucopyranosyl-1,1-sorbitol) (may be referred to as "first crystalline mixture solid composition of the present invention" hereinafter).

According to the present invention, secondly, the above objects and advantages of the present invention are attained by a thin scale crystalline mixture solid composition which comprises α-D-glucopyranosyl-1,1-mannitol and α-D-glucopyranosyl-1,6-sorbitol (may be referred to as "second crystalline mixture solid composition of the present invention" hereinafter).

According to the present invention, thirdly, the above objects and advantages of the present invention are attained by a process for producing a crystalline mixture solid composition, comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader to knead and cool it so as to produce a composition, mixing the composition with a hydrophilic solvent, separating solid matter from a liquid, and removing water and the solvent from the solid matter (the above wt % is based on the total weight of the α-D-glucopyranosyl-1, 1-mannitol, α-D-glucopyranosyl-1,6-sorbitol and α-D-glucopyranosyl-1,1-sorbitol) (may be referred to as "first production process of the present invention" hereinafter).

According to the present invention, fourthly, the above objects and advantages of the present invention are attained by a process for producing a crystalline mixture solid composition, comprising the steps of mixing an aqueous solution containing 50 to 80 wt % of α-D-glucopyranosyl-1,1-mannitol, 1 to 50 wt % of α-D-glucopyranosyl-1,6-sorbitol and 0 to 20 wt % of α-D-glucopyranosyl-1,1-sorbitol with a hydrophilic solvent, separating the formed precipitate from a liquid, and removing water and the solvent from the precipitate (the above wt % is based on the total weight of the α-D-glucopyranosyl-1,1-mannitol, α-D-glucopyranosyl-1,6-sorbitol and α-D-glucopyranosyl-1,1-sorbitol) (may be referred to as "second production process of the present invention" hereinafter).

THE PREFERRED EMBODIMENT OF THE INVENTION

The present invention will be described in detail hereinbelow. A description is first given of the first production process and the first crystalline mixture solid composition of the present invention.

In the first production process, as described above, a solidified mixture containing 50 to 80 wt % of GPM, 1 to 50 wt % of GPS-6 and 0.01 to 20 wt % of GPS-1 is used as a raw material.

As the raw material is used a crystalline mixture solid composition produced by solidifying a mixed solution prepared by hydrogenating a mixture of isomaltulose and trehalulose obtained by causing a transferase to act on cane sugar. In the first production process, the crystalline mixture solid composition of the present invention is produced by mixing this composition with a hydrophilic solvent, separating solid matter from a liquid, and removing water and the solvent from the solid matter.

The preferred contents of isomaltulose and trehalulose before hydrogenation are 5 to 100 wt % and 0 to 95 wt %, respectively.

The crystalline mixture solid composition of the present invention is produced from a mixture containing isomaltulose and trehalulose produced from cane sugar through an isomerization reaction before hydrogenation as described above. Impurities may be separated from the mixture as the raw material.

The transferase is a bacteria which is generally used for the production of isomaltulose, an enzyme extracted from the bacteria, or an immobilized product thereof, such as a bacteria which belongs to the genus of Protaminobacter, Serratia, Erwinia, Klebsierra, Pseudomonas, Agrobacterium or Leuconostoc.

To solidify a mixed solution of GPM, GPS-6 and GPS-1 by using a kneader, it is preferably solidified as a powdery crystalline mixture solid composition by supplying it into an extruder (kneader) having a slender cooling/kneading zone, kneading, cooling and extruding it through a punching plate, and cooling and grinding the extruded product.

The above mixed solution is supplied at preferably approximately 70 to 140° C., more preferably approximately 90 to 130° C. in consideration of fluidity for achieving handling ease and control ease for the formation of a magma. The temperature of a cooled portion for the formation of a magma may be adjusted to a temperature at which crystallization heat generated can be removed, preferably 100° C. or less, more preferably 70° C. or less.

The feed rate of the mixed solution into the kneader differs according to the type and capacity of the kneader in use. For example, when the KRC kneader (2S) of Kurimoto Ironworks Co., Ltd. is used, the mixed solution may be fed at a rate of 2 to 50 kg/hr.

To produce the crystalline mixture solid composition of the present invention, a seed crystal may be used in combination with the raw material composition. The seed crystal used at this point may be a seed crystal with which the mixed solution of GPM, GPS-6 and GPS-1 is crystallized in the kneader, for example, a crystal powder having almost the same composition (GPM/GPS-6/GPS-1) as that of the raw material mixed solution, or a seed crystal obtained by recycling a crystalline mixture solid composition produced by the present invention. The addition rate of the seed crystal is preferably approximately 0.1 to 25 kg/hr. The amount of the seed crystal added is not particularly limited but it is generally approximately 2 to 50 wt %, preferably approximately 5 to 40 wt % based on the raw material in consideration of crystallization speed and cost.

The kneader which can be used in the present invention may be of a continuous or batch system. A closed type kneader which is capable of kneading and cooling at the same time and can extrude the kneaded product continuously from a discharge port after kneading and cooling is preferred. Examples of the kneader include an extruder, continuous kneader, mixtron and kneadex. Out of these, an extruder is preferred. Examples of the extruder include KRC kneader (of Kurimoto Ironworks, Co., Ltd.), double-screw extruder for food (of Nippon Steel Co., Ltd.) and double-screw cooking extruder (of W & P Co., Ltd. of Germany).

When a magma is to be discharged from a continuous kneader, the shape of the magma may be selected from noodle-like, ribbon-like, rod-like and plate-like shapes, out of which noodle-like and ribbon-like shapes are preferred in consideration of subsequent cooling and grinding steps. A punching plate installed at the discharge port preferably has a pore diameter of approximately 2 to 5 mm and a porosity of approximately 10 to 40%.

The cooling method is not particularly limited. For example, the magma discharged from the kneader may be directly exposed to cool air, the magma may be left at the room temperature or the magma may be cooled to approximately room temperature on a metal net belt with cool air.

The obtained crystalline mixture solid composition is powdered by grinding. The grinding method is not particularly limited and a commonly used grinder may be used to grind the crystalline mixture solid composition.

The thus obtained powdery crystalline mixture solid composition contains water equivalent to the water of crystallization of GPM, for example, and mixed with a hydrophilic solvent. Preferably, the hydrophilic solvent preferably has lower solvency for GPM and GPS-6 than solvency for GPS-1. Examples of the hydrophilic solvent are aliphatic alcohols having 1 to 4 carbon atoms, acetone, aliphatic carboxylic acids having 1 to 3 carbon atoms, acetonitrile and pyridine. They may be used alone or in combination of two or more. Out of these, ethanol, methanol, acetone and n-propanol are preferred and ethanol is particularly preferred as the hydrophilic solvent.

When ethanol is used as the hydrophilic solvent, the concentration of ethanol is preferably approximately 60 to 90%. The amount of the hydrophilic solvent at the time of mixing is preferably approximately 2 to 10 times the amount of the solid matter. As for the stirring time and stirring speed, when stirring is carried out using a 6-blade turbine, the stirring time is preferably approximately 10 to 180 minutes and the stirring speed is preferably approximately 10 to 300 rpm.

To separate the solid matter or precipitate from a liquid after mixing, a general separation method such as suction filtration or centrifugal separation is employed. The solid matter after separation may be granulated as it is or by a granulator which is generally used after it is dried and the solvent is removed as required.

The above first crystalline mixture solid composition of the present invention is advantageously produced by the first process of the present invention.

The first crystalline mixture solid composition of the present invention comprises GPS-1 in an amount of preferably 0.01 to 1.5 wt %, more preferably 0.01 to 1.0 wt %.

A description is subsequently given of the second production process and the second crystalline mixture solid composition of the present invention.

The second production process of the present invention differs from the first production process in the following points. The solid matter containing GPM, GPS-6 and GPS-1 is mixed with the hydrophilic solvent in the first production process whereas an aqueous solution containing GPM and GPS-6 and/or GPS-1 is mixed with the hydrophilic solvent in the second production process. Commercially available hydrogenated isomaltulose may be used in the second production process. This aqueous solution has a solids content of preferably about 10 to 90 wt %, more preferably 20 to 80 wt %, particularly preferably 50 to 70 wt %. To mix together the aqueous solution and the hydrophilic solvent, the hydrophilic solvent may be added to the aqueous solution, or the aqueous solution may be added to the hydrophilic solvent. Alternatively, they may be added and mixed together at the same time. It should be understood that the above description of the first production process is applied to what is not described of the second production process directly or with modifications which are obvious to one of ordinary skill in the art.

The above second crystalline mixture solid composition of the present invention, that is, a crystalline mixture solid composition which is an aggregate of thin scale crystal particles is advantageously produced by the second production process of the present invention.

When the second crystalline mixture solid composition of the present invention contains GPS-1, the amount of GPS-1 is preferably 5 wt % or less, more preferably 2 wt % or less, much more preferably 1 wt % or less.

Preferably, the second crystalline mixture solid composition of the present invention comprises particles having a particle diameter of 60 Tyler mesh or less in an amount of at least 70 wt % of the total. The specific surface area of the second crystalline mixture solid composition is preferably 0.5 to 5.0 m$^2$/g, more preferably 0.5 to 2.0 m$^2$/g.

The packed bulk density (apparent specific gravity) of the second crystalline mixture solid composition of the present invention is preferably 0.2 to 0.6 g/cc, more preferably 0.3 to 0.5 g/cc.

When the second crystalline mixture solid composition of the present invention was observed through a ×500 or ×1,000 scanning electron microscope, a thin scale crystal structure was observed. When the second crystalline mixture solid composition of the present invention was compared with a solidified product of the raw material of the first crystalline mixture solid composition of the present invention and commercially available hydrogenated isomaltulose, it was confirmed that the composition differed from them in surface structure. It is also considered from the measurement results obtained by an X-ray diffraction measuring instrument and differential scanning calorimeter that the second crystalline mixture solid composition of the present invention has a different crystal structure from that of the prior art.

According to the present invention, there can be obtained a high-quality powdery or granular crystalline mixture solid composition which is easy to handle and soluble.

The present invention will be described in detail hereinbelow with reference to Examples and Comparative Examples. "%" in the Examples means "wt %".

EXAMPLES

Example 1

(Process)

(1) A sugar alcohol mixed solution containing 56.0% of GPM, 37.5% of GPS-6, 3.0% of GPS-1 and 3.5% of other sugars (mainly sorbitol and mannitol) was concentrated to a solids content of 94% and this concentrated solution was injected into a continuous closed kneader (S2-KRC kneader: manufactured by Kurimoto Ironworks, Co., Ltd., jacket temperature of 10° C., revolution of 60 rpm) together with 20 wt % of a seed crystal (trade name: ISOMALT TypeM, manufactured by Palatinit Co., Ltd.; spherical solid grain having a diameter of 0.5 to 4.5 mm and containing about 52.3% of GPM and about 47.1% of 1,6-GPS) based on the total amount while it was maintained at 120° C., kneaded and cooled. The kneaded product was extruded at a rate of 18 kg/hr through a punching plate having a diameter of 5 mm, and the extruded product was cooled and ground by a grinder (POWER MILL (TYPE P-3): manufactured by Showa Kagaku Kikai Kosakusho Co., Ltd.) to prepare a powdery crystalline mixture solid composition having a water content of 5.7%. (2) 100 g of the powdery crystalline mixture solid composition obtained in (1) above was added to 350 g of a 80% ethanol aqueous solution contained in a flask and stirred at 30° C. for 30 minutes, and the obtained slurry was separated into solid matter (powder) and a liquid by suction/filtration. The recovered solid matter was dried with a drier heated at 60° C. for 180 minutes to remove the solvent to obtain a powdery crystalline mixture solid composition having no moisture absorption.

(Results)

The sugar composition, solids content and solids yield of the obtained powdery crystalline mixture solid composition are shown in Table 1.

TABLE 1

|  | sugar composition (% · solids content) | | | solids content (%) | solids yield (%) |
| --- | --- | --- | --- | --- | --- |
|  | GPM | GPS-6 | GPS-1 | other sugars |  |  |
| raw material | 56.0 | 37.5 | 3.0 | 3.5 | 94.3 | — |
| Ex. 1 | 59.4 (59.8) | 39.1 (39.3) | 0.9 (0.9) | 0.6 | 94.0 | 89.0 |

Ex.: Example
*The figures within the parentheses in the table are the proportions of GPM, GPS-6 and GPS-1.

Example 2

(Process)

155.5 g of an aqueous solution obtained by concentrating the raw material sugar alcohol solution used in Example 1 to a solids content of 60% was added to 590.9 g of a 88% ethanol aqueous solution (final ethanol concentration was 80%). They were stirred at 30° C. for 30 minutes and the resulting solution was separated into a precipitate and a liquid by suction/filtration. The recovered precipitate was dried in the same manner as in Example 1 to obtain a powdery crystalline mixture solid composition having no moisture absorption.

(Results)

The sugar composition, solids content and solids yield of the obtained powdery crystalline mixture solid composition are shown in Table 2.

TABLE 2

|  | sugar composition (% · solids content) | | | solids content (%) | solids yield (%) |
| --- | --- | --- | --- | --- | --- |
|  | GPM | GPS-6 | GPS-1 | other sugars |  |  |
| raw material | 56.0 | 37.5 | 3.0 | 3.5 | 60.0 | — |
| Ex. 2 | 60.3 (58.6) | 41.9 (40.7) | 0.7 (0.7) | 2.8 | 99.0 | 81.8 |

Ex.: Example
*The figures within the parentheses in the table are the proportions of GPM, GPS-6 and GPS-1

Example 3

(Process)

63.5 g of an aqueous solution obtained by concentrating the raw material sugar alcohol solution used in Example 1 to a solids content of 70% was cooled to 30° C. and 136.5 g of a 91.2% ethanol aqueous solution (final ethanol concentration was 80%) was added to the aqueous solution over 60 minutes under stir. After the addition of the ethanol aqueous solution, the resulting solution was separated into a precipitate and a liquid by centrifugal filtration. The recovered precipitate was dried in the same manner as in Example 1 to obtain a powdery crystalline mixture solid composition having no moisture absorption.

(Results)

The sugar composition, solids content and solids yield of the obtained powdery crystalline mixture solid composition are shown in Table 3.

TABLE 3

|  | sugar composition (% · solids content) | | | solids content (%) | solids yield (%) |
| --- | --- | --- | --- | --- | --- |
|  | GPM | GPS-6 | GPS-1 | other sugars |  |  |
| raw material | 56.0 | 37.5 | 3.0 | 3.5 | 60.0 | — |
| Ex. 3 | 57.6 (61.3) | 35.6 (37.9) | 0.8 (0.8) | 6.0 | 93.8 | 90.5 |

Ex.: Example
*The figures within the parentheses in the table are the proportions of GPM, GPS-6 and GPS-1

Example 4 and Comparative Examples 1 and 2

(Process)

Pt-Pb was deposited on the powdery crystalline mixture solid composition obtained in Example 2, a solidified product of the raw material sugar alcohol mixed solution used in Example 1 (composition X) and a commercially available hydrogenated isomaltulose powder (composition Y) for 60 seconds and the obtained products were observed through a scanning electron microscope (S-4300: Hitachi, Ltd.) under a voltage of 1 kV.

(Results)

Figure 1:
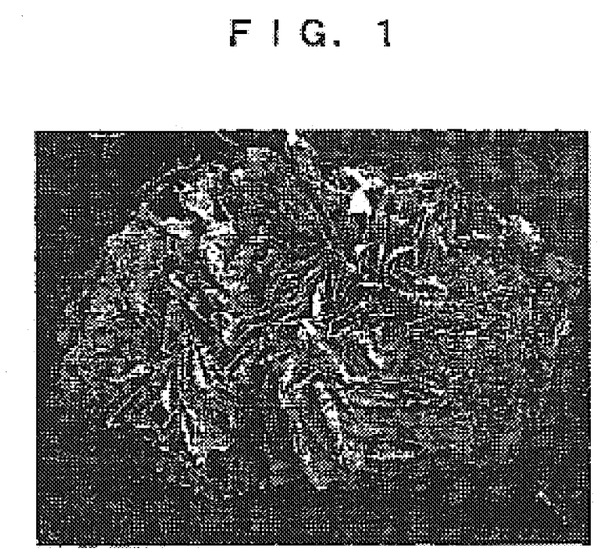
FIG. 1 is an electron photomicrographic diagram of a crystalline mixture solid composition obtained in Example 3 (magnification of ×500)
Figure 2:
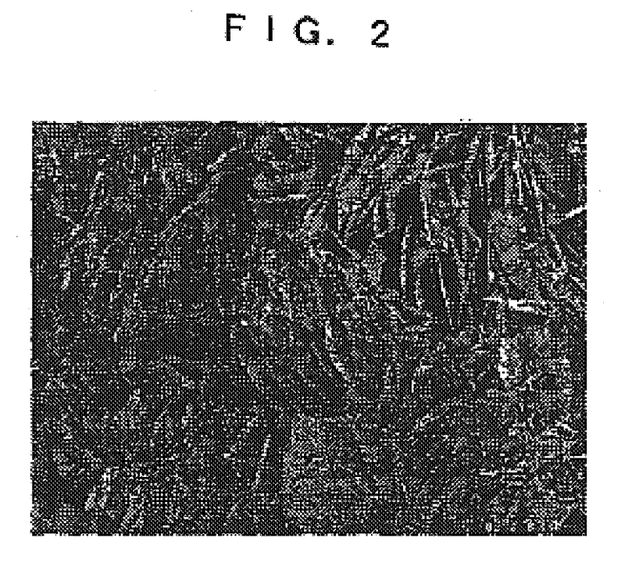
FIG. 2 is an electron photomicrographic diagram of a crystalline mixture solid composition obtained in Example 3 (magnification of ×1,000)
Figure 3:
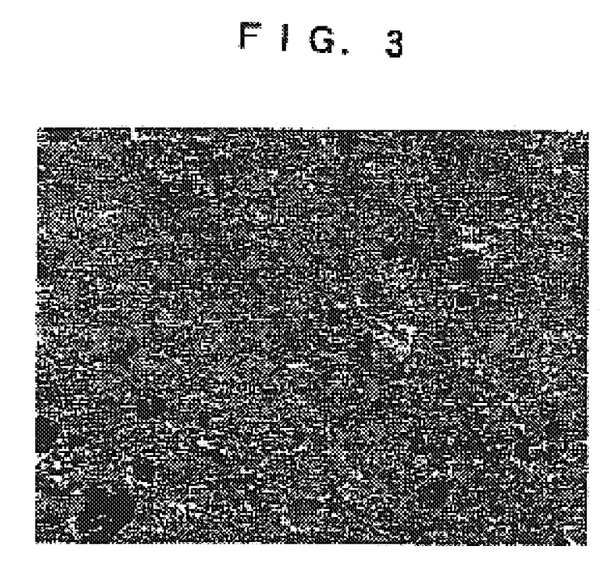
FIG. 3 is an electron photomicrographic diagram of composition X (magnification of ×500)
Figure 4:
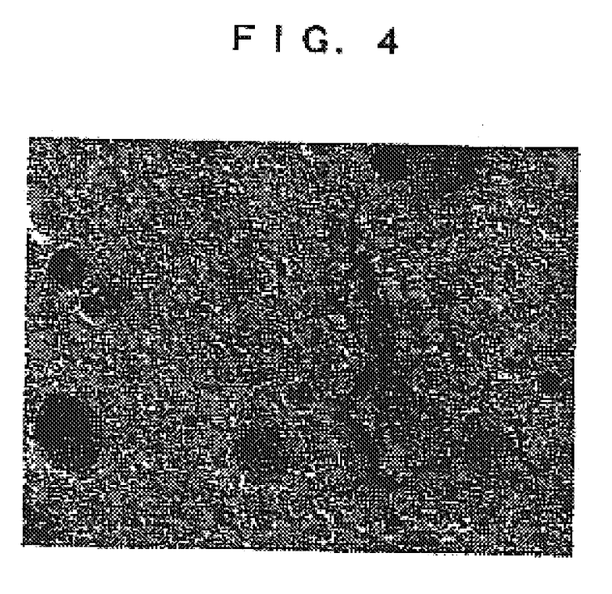
FIG. 4 is an electron photomicrographic diagram of composition X (magnification of ×1,000)
Figure 5:
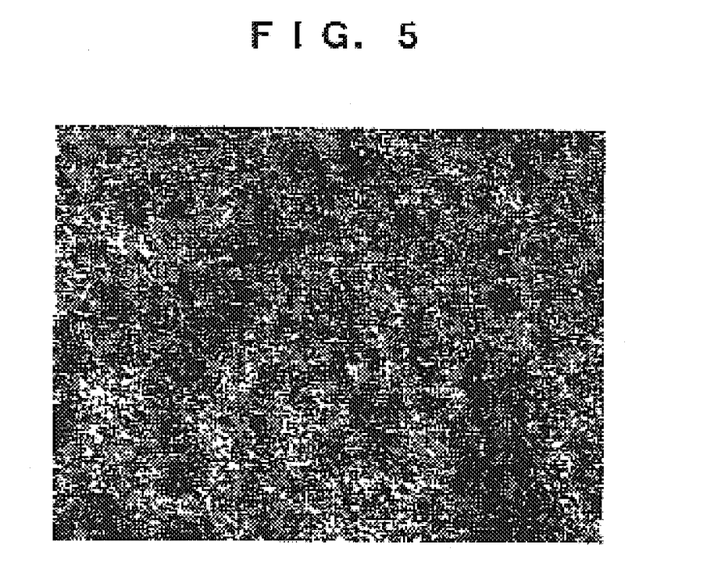
FIG. 5 is an electron photomicrographic diagram of composition Y (magnification of ×X500)
Figure 6:
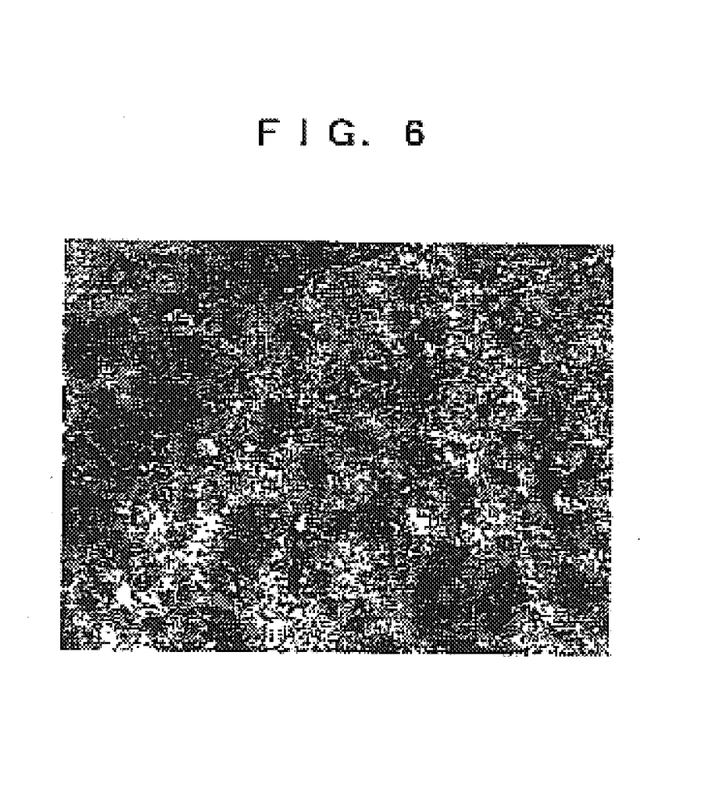
FIG. 6 is an electron photomicrographic diagram of composition Y (magnification of X1,000)

It was confirmed that the crystalline mixture solid composition obtained in Example 2 consisted of homogeneous thin scale crystals. FIG. 1 and FIG. 2 show ×500 and ×1,000 electron photomicrographs of the composition. FIG. 3 and FIG. 4 show ×500 and ×1,000 electron photomicrographs of Comparative Example 1 and FIG. 5 and FIG. 6 show ×500 and ×1,000 electron photomicrographs of Comparative Example 2.

Example 5 and Comparative Examples 3 and 4

The powdery crystalline mixture solid composition obtained in Example 2, the composition X and the composition Y were ground and sieved to measure the specific surface area and packed bulk density (apparent specific gravity) of what passed through a 60-mesh sieve.

(Method)

Specific Surface Area

The sample was dried at room temperature for 1 hour and used for the measurement of its specific surface area with the Monosobe MS-17 (manufactured by Yuasa Ionics Co., Ltd.).

Packed Bulk Density (Apparent Specific Gravity)

This was measured using a powder tester (PT-N: manufactured by Hosokawa Micron Co., Ltd.) (180 times of tapping).

(Results)

The obtained results are shown in Table 4.

TABLE 4

|  | Ex. 5 | C. Ex. 3 | C. Ex. 4 |
| --- | --- | --- | --- |
| specific surface area (m²/g) | 0.91 | 0.14 | 0.40 |
| packed bulk density (g/cc) (apparent specific gravity) | 0.41 | 0.65 | 0.79 |

Ex.: Example
C.Ex.: Comparative Example
*Each value is the mean of three measurement values.

Test Example
(Measurement with X-ray Diffraction Measuring Instrument)

Figure 7:
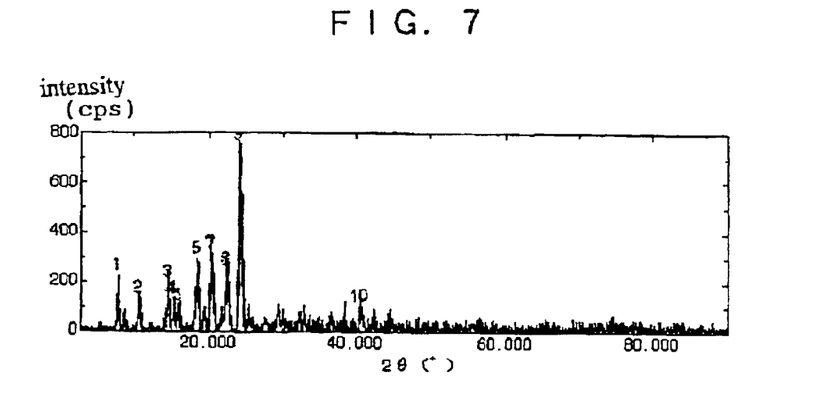
FIG. 7 is an X-ray diffraction diagram of a crystalline mixture solid composition obtained in Example 2.
Figure 8:
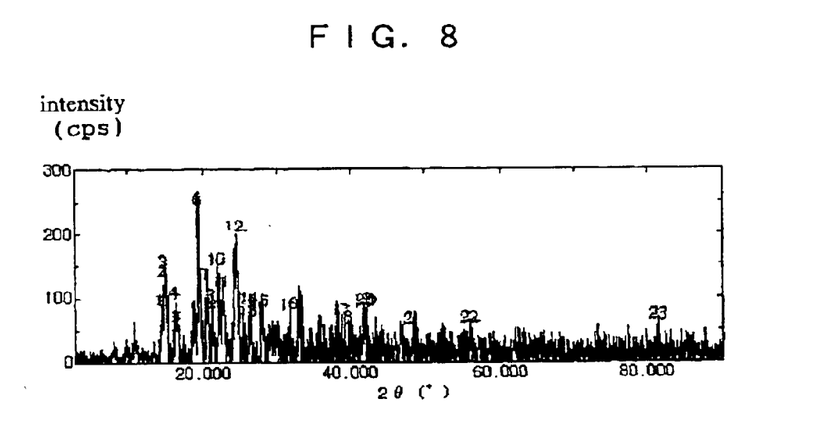
FIG. 8 is an X-ray diffraction diagram of composition X.
Figure 9:
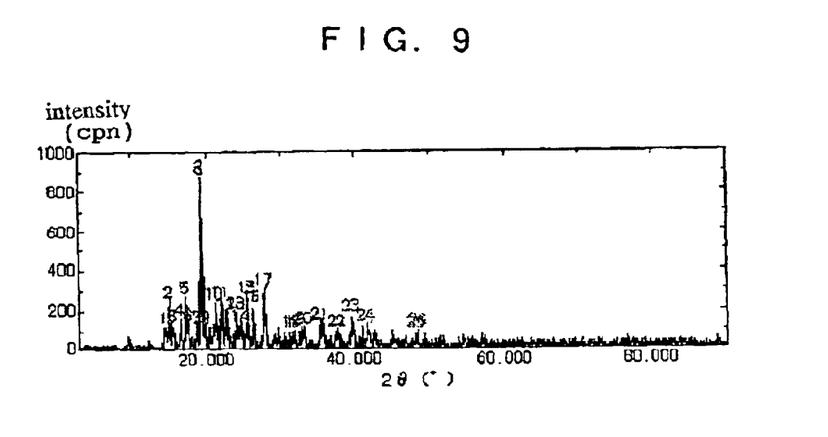
FIG. 9 is an X-ray diffraction diagram of composition Y.

The powdery crystalline mixture solid composition obtained in Example 2, the crystalline mixture solid composition of Comparative Example 1 and the hydrogenated isomaltulose powder of Comparative Example 2 were measured with an X-ray diffraction measuring instrument (MiniFlex: manufactured by Rigaku Co., Ltd.) at a scanning axis of θ/2θ, a measurement angle of 3 to 90° and a sampling axis of 0.01°. The measurement results are shown in FIG. 7, FIG. 8 and FIG. 9.

(Measurement with Differential Scanning Calorimeter)

Figure 10:
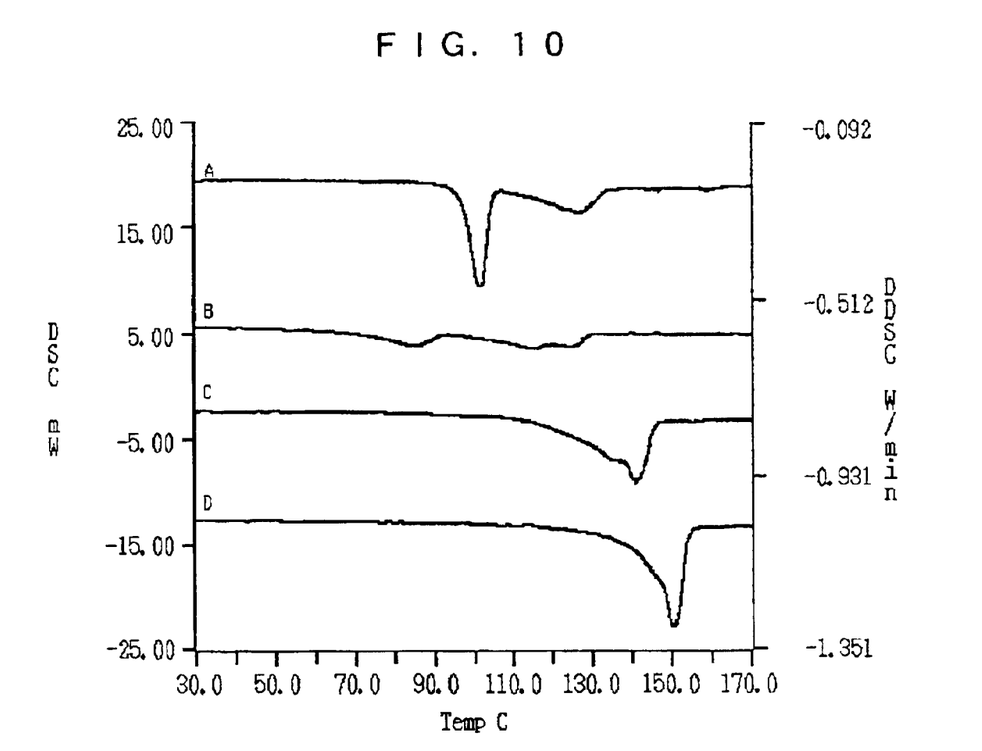
FIG. 10 is a differential scanning calorimeter analytical diagram of a crystalline mixture solid composition.

The powdery crystalline mixture solid compositions obtained in Examples 1 and 2, the crystalline mixture solid composition of Comparative Example 1 and the hydrogenated isomaltulose powder of Comparative Example 2 were dried at normal temperature under vacuum for 1 hour, placed in a closed sample container (made from Ag, 15 μl) and measured with a differential scanning calorimeter (DSC6200: Seiko Instruments Co., Ltd.) at a temperature range of 30 to 200° C. and a temperature elevation rate of 4° C./min. The measurement results are shown in FIG. 10. In FIG. 10, letters A, B, C and D denote the composition Y, composition X, crystalline mixture solid composition obtained in Example 1 and crystalline mixture solid composition obtained in Example 2, respectively.

According to the present invention, there can be provided a crystalline mixture solid composition which rarely has moisture absorption, is easy to handle and dissolve, and comprises GPM and GPS-6 and/or a small amount of GPS-1 in an extremely short period of time with small-scale equipment by a process which can save power and does take much time and labor.

What is claimed is:

1. A crystalline mixture solid composition comprising α-D-glucopyranosyl-1,1-mannitol, α-D-glucopyranosyl-1,6-sorbitol and 0.01 to 1.5 wt % of α-D-glucopyranosyl-1,1-sorbitol (the above wt % is based on the total weight of the α-D-glucopyranosyl-1,1-mannitol, α-D-glucopyranosyl-1,6-sorbitol and α-D-glucopyranosyl-1,1-sorbitol).

2. The crystalline mixture solid composition of claim 1 produced by a process comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader to knead and cool it so as to produce a composition, mixing the composition with a hydrophilic solvent, and separating solid matter from a liquid (the above wt % is based on the total weight of the α-D-glucopyranosyl-1,1-mannitol, α-D-glucopyranosyl-1,6-sorbitol and α-D-glucopyranosyl-1,1-sorbitol).

3. The crystalline mixture solid composition of claim 2 which comprises 0.01 to 1.5 wt % α-D-glucopyranosyl-1,1-sorbitol.

4. The crystalline mixture solid composition of claim 1 produced by a process comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader having a thin and long cooling/kneading zone to knead and cool it, extruding the kneaded product through a punching plate, cooling and grinding the extruded molded product to produce a powdery crystalline mixture solid composition, mixing the composition with a hydrophilic solvent, and separating solid matter from a liquid (the above wt % is based on the total weight of the α-D-glucopyranosyl-1,1-mannitol, α-D-glucopyranosyl-1,6-sorbitol and α-D-glucopyranosyl-1,1-sorbitol).

5. The crystalline mixture solid composition of claim 4 which comprises 0.01 to 1.5 wt % α-D-glucopyranosyl-1,1-sorbitol.

6. The crystalline mixture solid composition of claim 1 produced by a process comprising the steps of mixing a hydrophilic solvent with an aqueous solution which comprises 50 to 80 wt % of α-D-glucopyranosyl-1,1-mannitol, 1 to 50 wt % of α-D-glucopyranosyl-1,6-sorbitol and 0 to 20 wt % of α-D-glucopyranosyl-1,1-sorbitol, and separating the formed precipitate from a liquid (the above wt % is based on the total weight of the α-D-glucopyranosyl-1,1-mannitol, α-D-glucopyranosyl-1,6-sorbitol and α-D-glucopyranosyl-1,1-sorbitol).

7. The crystalline mixture solid composition of claim 6 which comprises 0.01 to 1.5 wt % α-D-glucopyranosyl-1,1-sorbitol.

8. A crystalline mixture solid composition comprising 50 to 98 wt % of α-D-glucopyranosyl-1,1-mannitol, 1 to 50 wt % of α-D-glucopyranosyl-1,6-sorbitol and 0.01 to 1.5 wt % of α-D-glucopyranosyl-1,1-sorbitol (the above wt % is based on the total weight of the α-D-glucopyranosyl-1,1-mannitol, α-D-glucopyranosyl-1,6-sorbitol and α-D-glucopyranosyl-1,1-sorbitol).

9. The crystalline mixture solid composition of claim 8 produced by a process comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader to knead and cool it so as to produce a composition, mixing the composition with a hydrophilic solvent, and separating solid matter from a liquid (the above wt % is based on the total weight of the α-D-glucopyranosyl-1,1-mannitol, α-D-glucopyranosyl-1,6-sorbitol and α-D-glucopyranosyl-1,1-sorbitol).

10. The crystalline mixture solid composition of claim 9 which comprises 0.01 to 1.5 wt % α-D-glucopyranosyl-1,1-sorbitol.

11. The crystalline mixture solid composition of claim 8 produced by a process comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader having a thin and long cooling/kneading zone to knead and cool it, extruding the kneaded product through a punching plate, cooling and grinding the extruded molded product to produce a powdery crystalline mixture solid composition, mixing the composition with a hydrophilic solvent, and separating solid matter from a liquid (the above wt % is based on the total weight of the α-D-glucopyranosyl-1,1-mannitol, α-D-glucopyranosyl-1,6-sorbitol and α-D-glucopyranosyl-1,1-sorbitol).

12. The crystalline mixture solid composition of claim 11 which comprises 0.01 to 1.5 wt % α-D-glucopyranosyl-1,1-sorbitol.

13. The crystalline mixture solid composition of claim 8 produced by a process comprising the steps of mixing a hydrophilic solvent with an aqueous solution which comprises 50 to 80 wt % of α-D-glucopyranosyl-1,1-mannitol, 1 to 50 wt % of α-D-glucopyranosyl-1,6-sorbitol and 0 to 20 wt % of α-D-glucopyranosyl-1,1-sorbitol, and separating the formed precipitate from a liquid (the above wt % is based on the total weight of the α-D-glucopyranosyl-1,1-mannitol, α-D-glucopyranosyl-1,6-sorbitol and α-D-glucopyranosyl-1,1-sorbitol).

14. The crystalline mixture solid composition of claim 13 which comprises 0.01 to 1.5 wt % α-D-glucopyranosyl-1,1-sorbitol.

15. A crystalline mixture solid composition which is thin scale and comprises α-D-glucopyranosyl-1,1-mannitol and α-D-glucopyranosyl-1,6-sorbitol.

16. The crystalline mixture solid composition of claim 15 which has a specific surface area of 0.1 to 5.0 m²/g.

17. The crystalline mixture solid composition of claim 15 produced by a process comprising the steps of mixing a hydrophilic solvent with an aqueous solution which comprises 50 to 80 wt % of α-D-glucopyranosyl-1,1-mannitol, 1 to 50 wt % of α-D-glucopyranosyl-1,6-sorbitol and 0 to 20 wt % of α-D-glucopyranosyl-1,1-sorbitol, and separating the formed precipitate from a liquid (the above wt % is based on the total weight of the α-D-glucopyranosyl-1,1-mannitol, α-D-glucopyranosyl-1,6-sorbitol and α-D-glucopyranosyl-1,1-sorbitol).

18. The crystalline mixture solid composition of claim 17 which has a specific surface area of 0.1 to 5.0 m²/g.

19. A process for producing a crystalline mixture solid composition, comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader to knead and cool it so as to produce a composition, mixing the composition with a hydrophilic solvent, and separating solid matter from a liquid (the above wt % is based on the total weight of the α-D-glucopyranosyl-1,1-mannitol, α-D-glucopyranosyl-1,6-sorbitol and α-D-glucopyranosyl-1,1-sorbitol).

20. The process for producing a crystalline mixture solid composition according to claim 19, wherein the hydrophilic solvent is ethanol.

21. The process for producing a crystalline mixture solid composition according to claim 19, wherein the hydrophilic solvent is an ethanol aqueous solution having a concentration of 60 to 90%.

22. A process for producing a crystalline mixture solid composition, comprising the steps of supplying a composition comprising 50 to 80 wt % of α-D-glucopyranosyl-1,1-mannitol, 1 to 50 wt % of α-D-glucopyranosyl-1,6-sorbitol and 0.01 to 20 wt % of α-D-glucopyranosyl-1,1-sorbitol into a kneader having a thin and long cooling/kneading zone to knead and cool it, extruding the kneaded product through a punching plate, cooling and grinding the extruded molded product to produce a powdery crystalline mixture solid composition, mixing the composition with a hydrophilic solvent, and separating solid matter from a liquid (the above wt % is based on the total weight of the α-D-glucopyranosyl-1,1-mannitol, α-D-glucopyranosyl-1,6-sorbitol and α-D-glucopyranosyl-1,1-sorbitol).

23. The process for producing a crystalline mixture solid composition according to claim 22, wherein the hydrophilic solvent is ethanol.

24. The process for producing a crystalline mixture solid composition according to claim 22, wherein the hydrophilic solvent is an ethanol aqueous solution having a concentration of 60 to 90%.

25. A process for producing a crystalline mixture solid composition, comprising the steps of mixing a hydrophilic solvent with an aqueous solution which comprises 50 to 80 wt % of α-D-glucopyranosyl-1,1-mannitol, 1 to 50 wt % of α-D-glucopyranosyl-1,6-sorbitol and 0 to 20 wt % of α-D-glucopyranosyl-1,1-sorbitol, and separating the formed precipitate from a liquid (the above wt % is based on the total weight of the α-D-glucopyranosyl-1,1-mannitol, α-D-glucopyranosyl-1,6-sorbitol and α-D-glucopyranosyl-1,1-sorbitol).

26. The process for producing a crystalline mixture solid composition according to claim 25, wherein the hydrophilic solvent is ethanol.

27. The process for producing a crystalline mixture solid composition according to claim 25, wherein the hydrophilic solvent is an ethanol aqueous solution having a concentration of 60 to 90%.

* * * * *